United States Patent [19]

Merrell et al.

[11] Patent Number: 4,539,428

[45] Date of Patent: Sep. 3, 1985

[54] PREPARATION OF DIAMINODIPHENYL ETHERS

[75] Inventors: Philip H. Merrell, Arnold; Michael F. Ellis, Hazelwood, both of Mo.

[73] Assignee: Mallinckrodt, Inc., St. Louis, Mo.

[21] Appl. No.: 376,478

[22] Filed: May 10, 1982

[51] Int. Cl.$^3$ ............................................. C07C 85/11
[52] U.S. Cl. ..................................... 564/430; 564/423
[58] Field of Search ................................. 564/430, 423

[56] References Cited

U.S. PATENT DOCUMENTS

| | | | |
|---|---|---|---|
| 1,574,337 | 2/1926 | Bogert | 564/430 |
| 3,140,316 | 7/1964 | Towle | 564/430 X |
| 4,222,962 | 9/1980 | Pellegrin | 564/430 |

FOREIGN PATENT DOCUMENTS 0992991  7/1976  Canada ................................. 564/430

Primary Examiner—Paul F. Shaver
Attorney, Agent, or Firm—R. G. Jackson; L. N. Goodwin; R. J. Klostermann

[57] ABSTRACT

Diaminodiphenyl ethers (DADPE's) are prepared by refluxing sodium or potassium aminophenate with chloronitrobenzene in dimethylformamide. The reaction mixture is hydrogenated directly without isolating the resulting intermediate product, aminophenyl-nitrophenyl ether, to form the corresponding DADPE, e.g., oxydianiline (ODA). The DADPE is crystallized from the hydrogenated reaction mixture in the presence of an aliphatic alcohol, which may be added to the reaction mixture prior to, during, or after hydrogenation. The resulting crystallized DADPE is typically of high purity and excellent color.

6 Claims, No Drawings

PREPARATION OF DIAMINODIPHENYL ETHERS

BACKGROUND

This invention relates to preparation of diaminodiphenyl ethers, and more particularly to preparation of bis(aminophenyl) ethers (e.g. oxydianiline, hereinafter sometimes referred to as ODA).

Various bis(aminophenyl) ethers (hereinafter sometimes referred to collectively as BAPE's) are known to be valuable as bifunctional cross-linking and network-extending agents for polymeric resins, plastics and elastomers. There is a substantial demand by users of BAPE's for high-purity and substantially colorless commercial grade of BAPE products, especially such ODA products.

In Canadian Pat. No. 992,991 (incorporated herein by reference), Jamieson et al. describe and claim inter alia a process for preparing 4,4'-diaminodiphenyl ether (also known as 4,4'-oxydianiline or simply 4,4'-ODA) which comprises refluxing a mixture containing approximately equimolar amounts of p-aminophenol, p-chloronitrobenzene, and potassium carbonate in dimethylformamide, hydrogenating the resulting mixture in the presence of a catalyst, recovering the dimethylformamide (or DMF as it is commonly referred to) by distillation, and crystallizing 4,4'-diaminodiphenyl ether (i.e., 4,4'-ODA) from the residue. As described in Example 1 of the Canadian Patent, the residue (remaining after distilling to recover 80% of the DMF) was "drowned with water, filtered and reprecipitated" to give "crude 4,4'-oxydianiline" (4,4'-ODA). Example 3 of Jamieson et al. states that, after "cooling and removal of catalyst by filtration, 4,4'-ODA was isolated as a pink solid by drowning the reaction mixture, including the DMF, with water and filtering," the pink solid having melting point (m.p.) of 187°–189° C. As described in each of Examples 1–3 of the Canadian patent, recovery (i.e., crystallization or isolation) of the 4,4'-ODA product includes a step of drowning with water. In Example 4 Jamieson et al. teach that the 4,4'-ODA "was isolated in the usual way," excess p-aminophenol was removed, the resulting "light *pink* product" had "m.p. 188°–190° C.," and "*reprecipitation from n-butanol* gave a nearly colorless product, m.p. 190°–191° C.,"

Although the Jamieson et al. process for preparing 4,4'-ODA represents a substantial advance, there remains a substantial need in the art for an improved process for preparing 4,4'-ODA (and other bis(aminophenyl)ethers). There also remains a need for an improved process for making BAPE's, especially ODA, having high purity and/or better color properties.

DESCRIPTION OF THE INVENTION

It has now been found that BAPE's, including ODA, of high purity and eminently suitable color properties can be prepared in a simple and efficient manner by crystallizing ODA from DMF-containing liquid reaction mixture including an aliphatic alcohol. In the process of this invention, high-purity, (e.g., greater than 98% pure) BAPE's (including ODA) having eminently suitable color properties can be prepared without requiring either the step of drowning with water or the step of recrystallization from n-butanol.

Generally stated, the present invention provides in a first aspect thereof a process for preparing a high-purity bis(aminophenyl) ether product which comprises (a) refluxing sodium or potassium aminophenate with a halonitrobenzene in a liquid reaction medium comprising dimethylformamide to form an aminophenylnitrophenyl ether, (b) hydrogenating said ether in said medium to form the bis(aminophenyl)ether, and (c) crystallizing said bis(aminophenyl)ether product from said reaction medium by cooling the mixture in the presence of a precipitation-effective amount of an aliphatic alcohol.

In a second aspect, generally stated, this invention also provides a process for preparing a high-purity 4,4'-oxydianiline product which comprises (a) refluxing a mixture comprising approximately equimolar amounts of (i) p-aminophenol, (ii) p-chloronitrobenzene, and (iii) potassium carbonate in a liquid medium comprising dimethylformamide, (b) hydrogenating the resulting mixture in the presence of a catalyst, (c) optionally recovering the dimethylformamide by distillation, and (d) crystallizing said 4,4'-oxydianiline product from the residue by cooling in the presence of a precipitation-effective amount of an aliphatic alcohol.

The present invention provides improvements over prior processes of the type described in the Canadian patent referenced above.

DETAILED DESCRIPTION OF THE INVENTION AND OF THE MANNER AND PROCESS OF MAKING AND USING IT

In a preferred embodiment of the invention, a mixture of p-aminophenol, potassium carbonate, p-chloronitrobenzene and dimethylformamide is refluxed in an inert atmosphere until reaction is substantially complete. The resulting product is 4-amino-4'nitrophenyl ether:

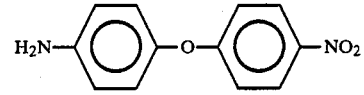

Typically, this intermediate product is at least substantially free of p-dimethylaminonitrobenzene.

Next, a suitable catalyst, e.g., Pd/carbon catalyst and preferably Pt/carbon catalyst, is added to the reaction mixture and hydrogenation of the intermediate product is thereafter effected, thereby reducing the nitro group to an amino group. The resulting product is 4,4'-diaminodiphenyl ether, also known as 4,4'-oxydianiline or, simply, 4,4'-ODA:

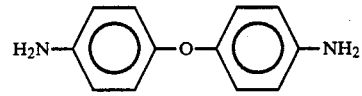

Either o-aminophenol or m-aminophenol may be substituted for the p-aminophenol, in which case the resulting product will have the amine group from the aminophenol in the corresponding position. Other halonitrobenzenes may be substituted for p-chloronitrobenzene. The halogen atom may be in the m- or p- or o-position and may be, for example, chlorine or bromine. In this way a variety of diaminodiphenyl ether products may be produced using this invention. Although potassium carbonate is preferred, it may be replaced with sodium carbonate or a mixture of sodium and potassium carbonates.

If desired, the above aminophenol and carbonate reactants collectively can be replaced with sodium or potassium aminophenate, which can be formed in situ in accordance with the description in the Canadian patent by refluxing a mixture containing the desired aminophenol and a sodium base or potassium base, respectively.

In the crystallization step of this invention the aliphatic alcohol may be, and preferably is, a lower alkyl alcohol containing for example from 1 to about 3 or more carbon atoms. Suitable alcohols include, for example, methanol, ethanol, isopropanol and mixtures thereof. In general, ethanol is preferred. The alcohol may be present in an amount, for example, from about 5 to about 95% by volume based on the total volume of the alcohol-modified reaction mixture. On the same basis, the amount of alcohol is preferably from about 25% to about 75%, more preferably from about 45% to about 55%, by volume.

The alcohol employed in the crytallization step may be added to the reaction mixture at any suitable time. The alcohol may be added, for example, after the refluxing step and prior to, during, or after the hydrogenation step.

For further enhancement of the quality (including purity and color) of the ODA or other BAPE products, the process of this invention preferably further includes removing residual impurities from the crystallized product by washing same with an aliphatic alcohol-containing washing agent which may be an aliphatic alcohol or a mixture thereof with water. Suitable aliphatic alcohols for use in this optionally, but preferably, included washing step are those described above for use in the crystallization step. Alcohol-water mixtures for use in the washing step preferably include at least 40% by volume of the alcohol employed.

The washing agent may include the alcohol in an amount, for example, from about 40% to about 100% by volume, preferably from about 50% to about 80% by volume, and more preferably from about 65% to about 75% by volume. The generally preferred washing-agent alcohol is ethanol.

The washing agent may be employed in any amount effective for further increasing the quality of the ODA or other BAPE product. In general, up to 10 or more milliliters (ml.) of washing agent may be used per gram (dry basis) of product. Preferably, about 0.5 to about 2 ml. of washing agent will be used on the same basis.

The crystallized product may be separated from the reaction mixture using known separation or recovery methods, e.g., filtration, centrifuging, and the like. If desired, the separated product may be dried under any suitable drying conditions, e.g., drying in air at a temperature up to 105° C. or higher.

Washing is carried out, if employed, following recovery of the crystallized product from the reaction mixture.

Final ODA and other BAPE products prepared by the process of this invention have been found to contain above 98% of the BAPE per se and to be of excellent color properties.

The following non-limiting examples are given by way of illustrating the invention.

EXAMPLE 1

A reaction mixture containing 4-aminophenyl-4'-nitrophenyl ether (ANPE) was prepared substantially as described in Example 4 of Canadian Pat. No. 992,991 using para-chloronitrobenzene, para-aminophenol and potassium carbonate as reagents and N,N-dimethylformamide (DMF) as the liquid medium. The mixture contained 1.5 moles of product (ANPE) per 300 ml of DMF. The salts were filtered from the mixture and thereafter it was hydrogenated in a hydrogen atmosphere of about 60 psi using about 1g of 3% Pt/C as catalyst. After hydrogenation was complete, 250 ml of ethanol was added and the solution was allowed to cool to crystallize and precipitate a light tan 4,4'-oxydianiline product which was thereafter recovered by filtering and then washing with 400 ml of a mixture of water and ethanol containing 75% by volume ethanol. After drying in air for 1–2 hours at 80°–100° C., the ODA product was found to assay above 98% 4,4'-ODA by HPLC using a 4,4'-ODA standard that has been recrystallized several times to achieve essentially 100% purity. The ODA product was judged to be of eminently suitable purity and color properties for use in reacting with dianhydrides by well known methods to form polyetherimides.

EXAMPLE 2

To an ANPE-containing mixture prepared as in Example 1 was added 400 ml ethanol. The resulting ethanol-containing mixture was next hydrogenated as in Example 1, except using 1g 3% Pd/C as catalyst. After hydrogenation was complete, the reaction mixture was cooled to crystallize the ODA product out of solution in the presence of the ethanol crystallization/precipitation agent. After filtering the ODA product, the latter was then dissolved in dilute aqueous HCl and the catalyst was filtered out. The ODA was then precipitated out of the HCl solution by neutralizing to pH 5 or slightly above with dilute aqueous $NH_4OH$ and the ODA was thereafter filtered out of the neutralized solution. After drying as in Example 1, the resulting ODA product was found to assay above 98% 4,4'-ODA and have excellent color properties, including substantial freedom from pink tint.

EXAMPLE 3

The procedure of Example 1 was repeated except that 250 ml isopropyl alcohol was added in lieu of the ethanol and hydrogenation was effected using about 2 g 1% Pd/C as the catalyst. The resulting ODA product was found to analyze about 98% 4,4'-ODA and have substantially the same color properties as the ODA product prepared in Example 2.

When sodium carbonate is substituted for potassium carbonate in the above examples the yield falls from about 90% down to around 70%.

The amount of solvent that can be used varies over a wide range which is limited only by ease of manipulation and economy. The reaction can be carried out with the preferred herein claimed reactants in other water-miscible aliphatic amide solvents.

As various changes could be made in the above methods without departing from the scope of the invention, it is intended that all matter contained in the above description shall be interpreted as illustrative and not in a limiting sense.

What is claimed is:

1. A process for preparing a high-purity, 4,4'-diaminodiphenyl ether product containing above 98% of the 4,4'-diaminodiphenyl ether per se and having substantial freedom from pin tint which comprises (a) refluxing a reaction mixture comprising approximately equimolar amounts of (i) p-aminophenol, (ii) p-chloronitrobenzene, and (iii) potassium carbonate in a liquid medium comprising dimethylformamide, (b) hydrogenating the resulting mixture in the presence of a catalyst, (c) recovering the dimethylformamide by distillation, and (d) crystallizing the 4,4'-diaminodiphenyl ether product from the residue by cooling said reaction mixture in the presence of a precipitation-effective amount of an aliphatic alcohol selected from the group consisting of methanol, ethanol, and isopropanol.

2. The process of claim 1 wherein said alcohol is present in an amount from about 5 to about 95% by volume based on the total volume of the alcohol-modified reaction medium.

3. The process of claim 2, wherein said amount is from about 45 to about 55% by volume.

4. The process of claim 1 which further comprises removing residual impurities from the crystallized product by washing said product with a washing agent selected from aliphatic alcohol and an alcoholic mixture thereof with water, said alcoholic mixture containing at least 40% by volume of said aliphatic alcohol, subject to the proviso that the aliphatic alcohol included in said alcoholic mixture is selected from the group consisting of methanol, ethanol, and isopropanol.

5. The process of claim 1 wherein said alcohol is added to said reaction medium after the refluxing step and prior to or during the hydrogenating step.

6. The process of claim 1 wherein said alcohol is added to said reaction medium after the hydrogenating step.

* * * * *